United States Patent [19]
Schönharting et al.

[11] Patent Number: 5,990,103
[45] Date of Patent: Nov. 23, 1999

[54] COMBINATION PREPARATION FOR USE IN IMMUNOLOGICAL DISEASES

[75] Inventors: Martin Schönharting, Taunusstein; Stefan Müllner, Hochheim; Peter Zabel, Bad Segeberg, all of Germany

[73] Assignee: Hoechst Aktiengesllschaft, Frankfurt am Main, Germany

[21] Appl. No.: 08/793,417

[22] PCT Filed: Aug. 7, 1995

[86] PCT No.: PCT/EP95/03125

§ 371 Date: Feb. 25, 1997

§ 102(e) Date: Feb. 25, 1997

[87] PCT Pub. No.: WO96/05838

PCT Pub. Date: Feb. 29, 1996

[30] Foreign Application Priority Data

Aug. 25, 1994 [DE] Germany .............................. 44 30 128

[51] Int. Cl.⁶ ..................................................... A61K 31/55
[52] U.S. Cl. ......................... 514/211; 514/262; 514/263; 514/826; 514/885; 514/889
[58] Field of Search ................... 514/224.8, 355, 514/356, 826, 885, 889, 211, 262, 263

[56] References Cited

U.S. PATENT DOCUMENTS 4,855,300   8/1989   Mandi et al. .
5,670,506   9/1997   Leigh et al. ............................. 514/258

FOREIGN PATENT DOCUMENTS 0234262   2/1986   European Pat. Off. .
0490181   11/1990  European Pat. Off. .
0493682   11/1990  European Pat. Off. .
0544391   9/1991   European Pat. Off. .

OTHER PUBLICATIONS

Chemical Abstracts AN 19993:52043, Massaia et al, "Cyclosporin A and Dipyridamole: an effective combination against the generation of cytotoxic T lymphocytes.", Pharmacol. Res.(Jan. 1992), 26 (suppl. 2).

Khabar et al., The 9th Inter. Congress of Immunology; San Francisco CA., Jul. 23–29, 1995, "Pentoxifylline Selectively Potentiates Cyclosporin a (CYA)–Mediated Suppression of Mixed Lymphocyte Cytotoxicity (MLC) Among other Immunological Functions" # 5054.

Carrier et al., Transplantation Proceedings, 26(5): 2745–2746 (1994), "Effect of Pentoxifylline on Renal Toxicity of Cyclosporin: Preliminary Results".

Galdal et al., Biochem. Pharmacology, 33(17):2723–2726 (1984), Inhibition of the Thromboplastin Response of Endothelial Cells In Vitro.

Sarriá et al., Fundam. Clin. Pharmacol., 8:26–33 (1994), "The nicardipine–isoprenaline interaction in human and guinea–pig isolated airways".

Berkenboom et al., J. of Cardiovascular Pharmacol., 18(5):761–768 (1991) "Prevention of Cyclosporine A–Induced Vascular Toxicity by Pentoxifylline".

Stewart et al., Amer. J. of Clin. Oncol., 17(4): 313–316 (1994), "Addition of Pentoxifylline plus Nifedipine to Chemotherapy in Patients with Cisplatin–Resistant Cancers of the Lung and Other Sites".

Reece et al., Ann. Meeting of the Canadian Society for Clinical Investigation and the Royal College of Physicians and Surgeons of Canada, Sep. 11–14m 1992 "Chronic Graft–Versus–Host Disease (CGVHD) in Patients (PTS) Receiving Unrelated Donor (UD) Allogeneic Bone Marrow Transplants (ALLO BMTS) Incidence Risk Factors and Outcome".

Database Caplus on STN, AN 1991:143854, Sharpe et al, "Treatment of cutaneous hypersensitivity with topical calcium channel blockers", S. African, (corresponding to ZA 9006583), pub. Jul. 20, 1990.

Chemical Abstracts AN 1988:216 076, Hui et al, 1988.

Primary Examiner—Keith D. MacMillan
Attorney, Agent, or Firm—Foley & Lardner

[57] ABSTRACT

A combination preparation comprising a compound which has a phosphodiesterase-inhibiting action, and a compound which reduces the biologically effective intracellular $Ca^{2+}$ content, is suitable for the treatment of immunological diseases.

8 Claims, No Drawings

COMBINATION PREPARATION FOR USE IN IMMUNOLOGICAL DISEASES

This application is a 371 of PCT/EP/95/03175, filed Aug. 07, 1995 which claims priority to FED REP Germany Application p4430128.6-41 filed Aug. 25, 1994.

The invention relates to pharmaceutical combination preparations for the treatment of immunological diseases in the broadest sense, which determine syndromes differing in their causes or symptoms. These combination preparations are determined by the pharmacological mechanisms of action on which the individual components are each based, and can be characterized by an inhibitory action on phosphodiesterases combined with a lowering of the biologically effective intracellular $Ca^{2+}$ concentration.

The activation of immunocompetent cells, which is the basis of any immune response, proceeds via the so-called signal chain: An extracellular stimulus (e.g. a toxin, an antigen or else complement, inflammation mediators, arachidonic acid derivatives or other metabolic products) reaches the cell as an "information carrier" and transfers the material information—usually via suitable receptors—to the target cell. This information is transmitted inside the cell to the nucleus via various intermediate stages within the signal chain, the nucleus reacts to this stimulus with proliferation and/or the formation of specific activators and the immune response is thus initiated in an appropriate way. However, the individual steps in this intracellular transmission of the information are still poorly understood, particularly as there are obviously different paths which can be followed within the cell in order to trigger an immune response. Thus, for example, depending on the type of receptor and the subunits coupled thereto (guanine nucleotide-binding proteins or "G proteins"), inositol triphosphate ($IP_3$), diacylglycerol (DAG), phosphatidylcholine (PC) or phosphatidylinositol (PI) can be detected in the sequence, said compounds arising from a stimulus induced activation of phospholipase C or D and being associated with an increase in intracellular free $Ca^{2+}$, while an activation of phospholipase $A_2$ incurs the formation of arachidonic acid derivatives (prostaglandins, leukotrienes), which in turn can trigger their own stimulus via suitable receptors, with corresponding consequences. A second type of receptor is coupled via corresponding G proteins to adenylate cyclase (AC), the activation of which results in the formation of cyclic 3',5'-adenosine monophosphate (cAMP), while a third type seems to trigger effects which are again independent thereof (for survey see Roitt (ed.): Essential Immunology, Blackwell Scient. Publ. Oxford 1991, and Foreman, Fan (eds.). Textbook of Immunopharmacology, Blackwell Scient. Publ. Oxford 1994).

Both $Ca^{2+}$ and cAMP are thus important information transmitters (second messenger) in signal transduction, although the processes subsequently taking place inside the cell are so complex that it is impossible to make a general prediction of the resulting cytobiological events. In any case the majority of downstream activation phenomena seem to depend on phosphorylation steps in the cell, which in turn are regulated via corresponding protein kinases or phosphatases. Particular mention may be made here of protein kinase C (PKC), whose activity is controlled via DAG and $IP_3/Ca^{2+}$ in a concerted action, whereby the availability of intracellular free $Ca^{2+}$ takes on a key role in the cascade of cell activation, irrespective of the fact that usually the $Ca^{2+}$/calmodulin complex subsequently mediates the $Ca^{2+}$ effects (Hidaka et al.: Cell Calcium 13, 465–472 (1992); Kun et al.: Endocrin. Rev. 14, 40–58 (1993)). Phosphorylations do not have to lead to activations in every case, however, but can also induce inhibitory effects. Thus, for example, the cAMP-dependent protein kinase A (PKA) counter-acts cell activation in the way that really only the complex interplay of phosphorylation and dephosphorylation allows efficient regulation of cell activity and thereby makes it possible for the organism to react usefully to variable external influences (Sitkovsky et al.: Ann. NY Acad. Sci. 532, 350–358 (1988); Takayama et al.: J. Pharm. Sci. 78, 8–10 (1989)). One and the same substance can have both agonistic and antagonistic effects. Thus, for example, cAMP inhibits activation induced by interleukin-2 (IL-2) (Friedrich et al.: Eur. J. Immunol. 19, 1111–1116 (1979)); on the other hand, it not only potentiates IL-1-induced activation but, under certain circumstances, can even act as an IL-1 agonist itself (Shirakawa et al.: Proc. Natl. Acad. Sci. 85, 8201–8205 (1988); Schlegel-Hajuter et al.: Cell. Sign. 2, 489–496 (1990)). With such mechanistic considerations, however, it must not be forgotten that the appearance of a second messengers in response to a corresponding stimulus does not in itself allow any conclusions about its functional involvement; rather, this can also merely represent an epiphenomenon (Hansen et al.: Brit. J. Cancer 69, 291–298 (1994); Baumgold et al.: J. Neurochem. 58, 1754–1759 (1992)). This statement is supported by Example 3 of the present patent application, where it is shown that the effect of a phosphodiesterase inhibitor (pentoxifylline) definitely cannot always be explained by an increase in cAMP, but rather, under certain conditions, is to be sought in the general inhibitory action of this group of substances on dephosphorylation processes. Accordingly, the extent to which certain mechanisms can gain importance in signal transduction depends on a variety of factors; correspondingly unpredictable are the effects of substances which pharmacologically influence signal substances involved at various sites of the process, especially when they act in combination.

Substances with a phosphodiesterase-inhibiting action are known and some are already used in therapeutics. They represent a heterogeneous class of substances which are characterized in that they inhibit the cleavage of cyclic mononucleotides by phosphodiesterases (PDE), leading to a concentration of cAMP or cGMP inside the cell; it must be emphasized, however, that the inhibitory actions of PDE inhibitors (as already mentioned above) does not stop here but generally extends to a wide variety of enzymes having whatever type of phosphatase activity, with all the resulting consequences on the diverse regulatory (de)phosphorylation processes inside the cell. However, even as far as the narrower reaction of the cleavage of a phosphodiester bond is concerned, this reaction is catalyzed not by a single enzyme but by a whole enzyme system comprising at least 5 different families of isoenzymes and more than 20 individual enzymes (for survey see Beavo et al.: Trends Pharmacol. Sc. 11, 150–155 (1990)). As the underlying enzymatic reaction (=hydrolytic cleavage of a phosphoester bond) is always the same, all PDE inhibitors exhibit a correspondingly overlapping inhibitory action; thus there are e.g. PDE inhibitors, like theophylline, pentoxifylline or papaverine, which also very non specifically inhibit very different phosphodiesterases. However, even when PDE inhibitors are termed "specific" in the scientific literature, this merely indicates a certain preference for a particular family of isoenzymes without immediately implying a claim to exclusivity. There are many examples of this: Thus the $Ca^{2+}$/calmodulin-dependent PDE I cleaves both cGMP and cAMP and is inhibited e.g. by phenothiazine, vinpocetine or IBMX. The cGMP-stimulatable PDE II also cleaves cGMP and cAMP, but no selective inhibitors are known for this enzyme; this is in contrast to PDE III, which has an identical substrate specificity to PDE II but can be inhibited by cGMP and a large number of other substances. The sometimes considerable structural differences between PDE III inhibitors, such as cilostamide, milrinone, trequinsine, indolidane or quazinone, suggest that on the one hand there must be different inhibiting regions on PDE III, but that on the other hand there must also be a variety of isoenzymes in this PDE family. Other inhibitors to be found are PDE IV, which has a strong preference for the hydrolysis of cAMP, e.g. Ro 201724 and rolipram in the literature, while PDE V, which is specific for the cleavage of cGMP, is inhibited by zaprinast or dipyridamol.

Substances which can lower the content of biologically effective intracellular $Ca^{2+}$ are also known and are already frequently used in therapeutics. These include firstly the conventional calcium channel blockers, which—based on the knowledge of the various types of $Ca^{2+}$ channels—can be subdivided into dihydropyridines (e.g. nifedipine, nicardipine, nimodipine), phenylalkylamines (e.g. verapamil) and benzothiazepines (e.g. diltiazem) (for survey see Piepho: Hosp. Pharm. 26, 856–864 (1991); Luft et al.: Clin. Exp. Hypertens. 15, 1263–1276 (1993)) and specific drugs developed therefrom, such as isradipine, felodipine, diperdipine or amlodipine. However, atypical $Ca^{2+}$ channel blockers such as flunarizine, fluspirilene, pimozide, fantofarone, nicergoline or cyclandelate, or aminoglycoside-based antibiotics, such as neomycin, gentamycin or kanamycin, have also already reached clinical maturity in isolated cases. The aim of yet other preparations was to inhibit the release of $Ca^{2+}$ from its intracellular stores (Massingham et al.: Drugs Today 27, 459–477 (1991)). Examples of substances which comply with these requirements are ryanodine, dantrolene or TMB-8, but at the moment they only have experimental importance for studying the mechanism of action; exactly the same applies to HA 1077, although this not only inhibits the intracellular $Ca^{2+}$ mobilization but obviously also has direct $Ca^{2+}$ antagonistic effects. This leads up to the group of true calcium antagonists, which either capture free $Ca^{2+}$ ions direct via specific chelation, like EGTA and its derivatives (for survey see Grynkiewicz et al.: J. Biol. Chem. 260, 3340–3346 (1985)), or act as calmodulin antagonists. The latter include the naphthalenesulfonic acid derivatives W7, W12 and W13, calmidazolium or fluphenazine, as well as the group comprising cyclosporins or tacrolimus, although these first have to be bound to intracellular "immunophilins" before they can inhibit the $Ca^{2+}$/calmodulin-dependent enzyme calcineurin (a phosphatase) (Liu: Immunol. Today 14, 290–295 (1993)).

Combinations of so-called "PDE inhibitors" with so-called "calcium antagonists" in the broadest sense are also already known. This follows from the indications of both groups of substances, which in both cases concern predominantly the cardiovascular area, suggesting the idea of co-medication (EP-B-0 234 262). However, this relates exclusively to the treatment of circulatory disturbances on the basis of increased spasmolytic and microcirculatory effects of the combination, compared with the individual components, and makes no reference whatsoever to immunological questions, the use of the individual components in the immunological area—apart from a small number of exceptions like cyclosporin or tacrolimus—generally being ruled out because of incompatibility phenomena at the higher dosages which are then required (Fisher et al.: Drugs 46, 961–975 (1993)).

The use of PDE inhibitors (particular xanthine derivatives) together with so-called "calcium antagonists" (cyclosporin A or tacrolimus) is also described (EP 0 493 682, EP 0 490 181, WO 93/17684), but here the claims pertain exclusively to reducing the toxicity of said immunosuppressants. Such findings are known in the literature and, in particular, contain no indication whatsoever of any kind of intensification of the immunosuppressant effect of these special calmodulin antagonists by the PDE inhibitor used (see e.g. Brunner et al.: Renal Fail. 11, 97–104 (1989); Berkenboom et al.: J. Cardiovasc. Pharmacol. 18, 761–768 (1991); Rossi et al.: Drug Saf. 9, 104–131 (1993)).

It has now been found that a combination containing a compound which exerts an inhibitory action on phosphodiesterases, and a compound which reduces the biologically effective intracellular $Ca^{2+}$ content, has a superadditive immunosuppressant effect. The extent of this effect enables the application of this combination to be extended to areas which have so far been inaccessible to immunosuppressant therapy with the individual components because of intolerable incompatibility phenomena. At the same time it is assumed that the costs of therapy can be appreciably reduced by lowering the dose for an equivalent activity.

The invention therefore relates to a combination preparation comprising at least
1) one compound which has a phosphodiesterase-inhibiting action (so-called "PDE inhibitors"),
2) one compound which reduces the biologically effective intracellular $Ca^{2+}$ content (so-called calcium antagonists), and
3) one pharmaceutical excipient, affording a superadditive increase in the immunosuppressant action, to be used simultaneously, separately or at different times.

Examples of known compounds with a phosphodiesterase-inhibiting action are:
phenothiazine, vinpocetine, cilostamide, milrinone, trequinsine, indolidane. quazinone, Ro 201724, rolipram, zaprinast, dipyridamol, papaverine or xanthine derivatives such as pentoxifylline, theophylline or IBMX.

Examples of compounds which reduce the intracellular content of biologically effective $Ca^{2+}$ are,
1. specific $Ca^{2+}$ channel blockers (P-, L-, N-type), e.g. dihydropyridines such as nifedipine, nicardipine, nimodipine, NZ-105, S11568, amlodipine, felodipine, isradipine or diperdipine, phenylalkylamines such as verapamil, benzothiazepines such as diltiazem, atypical $Ca^{2+}$ channel blockers such as flunarizine, fluspirilene, pimozide, fantofarone, nicergoline or cyclandelate, or aminoglycoside-based antibiotics such as neomycin, gentamycin or kanamycin;
2. true $Ca^{2+}$ antagonists, e.g. 1,2-bis(2-aminoethoxyethane)-N,N,N'-,N'-tetraacetic acid (EGTA) or HA1077;
3. inhibitors of $Ca^{2+}$ release from intracellular stores, e.g. ryanodine, dantrolene, TMB-8 or HA1077; and
4. calmodulin inhibitors, e.g. naphthalenesulfonic acid derivatives, calmidazolium, fluphenazine, cyclosporins or tacrolimus.

The term "superadditive" is understood as meaning actions which are greater than the sum of the individual actions.

Preferred combination preparations contain pentoxifylline and nifedipine, pentoxifylline and diltiazem, pentoxifylline and verapamil or pentoxifytline and cyclosporin A.

The combination preparation according to the invention is suitable for example for the treatment of acute immunological events such as sepsis, allergy, graft-versus-host reactions and host-versus-graft reactions;

autoimmune diseases, especially rheumatoid arthritis, systemic lupus erythematosus and multiple sclerosis;

psoriasis, atopic dermatitis, asthma, urticaria, rhinitis and uveitis;

type II diabetes; and fibrosis of the liver, cystic fibrosis and colitis.

The combination preparation according to the invention can also include combination packs or compositions in which the components are placed side by side and can therefore be used simultaneously, separately or at different times on one and the same human or animal body.

The invention further relates to the use of a combination of a compound which has a phosphodiesterase-inhibiting action, and a compound which reduces the biologically effective intracellular $Ca^{2+}$ content, for the preparation of a drug affording a superadditive increase in the immunosuppressant action.

The invention further relates to a process for the manufacture of the combination preparation, characterized in that 1) a compound which has a phosphodiesterase-inhibiting action,
2) a compound which reduces the biologically effective intracellular $Ca^{2+}$ content, and
3) a pharmaceutical excipient are processed in conventional manner to a pharmaceutical form of administration.

The combination preparation according to the invention can be presented as a dosage unit in medicinal forms such as capsules (including micro-capsules, which do not generally contain a pharmaceutical excipient). tablets (including coated tablets and pills) or suppositories, it being possible when using capsules, for the capsule material to take over the function of the excipient and for the contents to be present e.g. as a powder, gel, emulsion, dispersion or solution. However, it is particularly advantageous and simple to prepare oral (peroral) formulations with the two active substance components 1) and 2), which contain the calculated amounts of the active substances together with any desired pharmaceutical excipient. It is also possible to use a formulation appropriate for rectal therapy (suppository). Further possibilities are transdermal application in the form of ointments or creams, the parenteral (intraperitoneal, subcutaneous, intravenous, intraarterial, intramuscular) injection or infusion of solutions or the oral administration of solutions containing the combinations according to the invention.

In addition to the active substances, ointments, pastes, creams and powders can contain the customary excipients, e.g. animal and vegetable fats, waxes, paraffins, starch, gum tragacanth, cellulose derivatives, polyethylene glycols, silicones, bentonite, talcum, zinc oxide, lactose, silicic acid, aluminum hydroxide, calcium silicate and powdered polyamide, or mixtures of these substances.

The tablets, pills or granules can be produced by conventional processes, such as compression, immersion or fluidized bed processes or pan coating, and contain excipients and other conventional adjuncts such as gelatin, agarose, starch (e.g. potato, maize or wheat starch), cellulose such as ethyl cellulose, silicon dioxide, various sugars such as lactose, magnesium carbonate and/or calcium phosphates. The coating solution normally consists of sugar and/or starch syrup and usually also contains gelatin, gum arabic, polyvinylpyrrolidone, synthetic cellulose esters, surface-active substances, plasticizers, pigments and similar additives appropriate to the state of the art. Any conventional flow regulator, liniment or lubricant, such as magnesium stearate, and any conventional release agent can be used to manufacture the medicinal forms.

The preparations preferably take the form of press-coated tablets or multilayer tablets, active component 2 being in the coating or core or in one layer and active component 1 being in the core or coating or in a different layer. The active substance components can also be in a depot form, adsorbed onto the sustained-release material or included in the sustained-release material (e.g. one based on cellulose or polystyrene resin, e.g. hydroxyethyl cellulose). A delayed release of the active substances can also be achieved by providing the relevant layer or compartment with conventional enteric coatings.

The dosage to be used naturally depends on various factors such as the organism to be treated (i.e. human or animal), age, weight, general state of health, severity of the symptoms, disease to be treated, possible accompanying diseases, (if present) type of concomitant treatment with other drugs, or frequency of the treatment. The dosages are generally administered several times a day and preferably once to three times a day. The amounts of individual active substance used are governed by the recommended daily dose of the individual active substance in question and should generally be from 10% to 100% of the recommended daily dose, preferably from 20% to 80% and especially 50%, in the combination preparation. The appropriate therapy with the combinations according to the invention thus consists e.g. in administering one, two or 3 single dosages of the combination preparations according to the invention comprising 1) 1 mg to 10 mg, preferably from 2 mg to 5 mg, of vinpocetine and
2) 20 mg to 80 mg, preferably 30 mg to 50 mg, of diltiazem, the amount naturally depending on the number of single dosages and also on the disease to be treated, and it also being possible for a single dosage to consist of several dosage units administered simultaneously. In the case of oral administration to an adult, the dose is generally at most 30 mg/day for vinpocetine (component 1) and at most 240 mg/day for diltiazem (component 2).

For all the in vitro tests, peripheral blood mononuclear cells (PBMC) were obtained from the blood of healthy donors by density gradient centrifugation in Ficoll-Hypaque (Pharmacia, Uppsala). This isolation step separated monocytes and lymphocytes from the other blood constituents. Further working-up of this PBMC fraction was carried out in accordance with the requirements of the test preparations described below.

EXAMPLE 1

After the PBMC had been washed in Hank's solution (HBSS), the number of cells was adjusted to $1 \times 10^6$ cells/ml with culture medium (RPMI-1640 supplemented with 10% (v/v) of heat-inactivated fetal calf serum and 1% (v/v) of penicillin/streptomycin (Biochrom, Berlin)). The resulting PBMC were incubated on microtiter plates together with phythemagglutinin (PHA, 5 $\mu$g/ml). The test substances dibutyryl-cAMP (db-cAMP) or nifedipine (Sigma, Munich) were added in concentrations of 0.01 $\mu$M to 100 $\mu$M (final concentration), either alone or in combination in HBSS. Incubation was carried out at 37° C. in 5% $CO_2$ with protection from the light. After 20 hours (h) (TNFα determination), 24 h (IL-2 determination) or 120 h (IFN$_Y$ determination), the cell supernatants were tested for cytokine release. TNFα was determined via its cytotoxicity to L929 cells, IL-2 was quantified via the proliferation of CTL-L6 cells and IFN$_y$ was determined using a sandwich ELISA.

Table 1 shows the inhibition of the PHA-induced release of cytokines (TNFα, IL-2, IFN$_Y$) from peripheral blood mononuclear cells by the exogenous addition of membrane-penetrating cAMP (dibutyryl-cAMP), a PDE inhibitor (pentoxifylline) and a $Ca^{2+}$ channel blocker (nifedipine), individually or in combination:

TABLE 1

| Test substance | Final concentration | TNFα | IL-2 % inhibition | IFN$_Y$ |
| --- | --- | --- | --- | --- |
| nifedipine | 10 μmol/l | 36 ± 9 | 23 ± 11 | 16 ± 6 |
| pentoxifylline | 50 μmol/l | 28 ± 10 | 14 ± 9 | 20 ± 9 |
| db-cAMP | 0.1 μmol/l | 31 ± 13 | 12 ± 4 | 15 ± 8 |
| nifedipine + pentoxifylline | 10 μmol/l 50 μmol/l | 82 ± 13 | 66 ± 15 | 75 ± 14 |
| nifedipine db-cAMP | 10 μmol/l 0.1 μmol/l | 87 ± 17 | 81 ± 14 | 74 ± 16 |

With the aid of the conventional calcium channel blocker nifedipine, Example 1 shows that a combination with the phosphodiesterase inhibitor pentoxifylline has a superadditive inhibitory effect on the formation of various cytokines relevant to the immune response, such as tumor necrosis factor a (TNFα), interleukin-1 (IL-1) or y-interferon (IFN$_y$), so a superadditive immunosuppressant effect of the combination can also be expected for in vivo conditions. If the pentoxifylline is replaced with a membrane-penetrating form of cAMP (dibutyryl-cAMP), similarly super-additive effects can be observed, suggesting that in the case of pentoxifylline under the chosen experimental conditions, the PDE-inhibiting effect of this substance (with a resulting intracellular increase in cAMP) does indeed have a role to play, with the consequence that these effects can also be transferred to other PDE inhibitors.

EXAMPLE 2

The following test examined the dependence of the inhibition of PHA-induced cytokine formation on the type of so-called "calcium antagonist" added. The experimental test preparation corresponded to that of Example 1 in every respect. The test substances pentoxifylline, nifedipine, verapamil and diltiazem (Sigma, Munich) were added in final concentrations of 0.01 μM to 100 μM. the final concentration range for cyclosporin A (Sandoz, Basle) extended from 5 ng/ml to 50 ng/ml. TNFα was selected as the representative cytokine and was quantified as in Example 1.

Table 2 shows the percentage inhibition of the PHA-induced release of TFNα from peripheral blood mononuclear cells in the presence of different "calcium antagonists", either individually or in combination with pentoxifylline.

TABLE 2

|  | Nifedipine 10 μmol/l | Diltiazem 10 μmol/l | Verapamil 10 μmol/l | Cyclosporin A 25 ng/ml |
| --- | --- | --- | --- | --- |
| test substance alone | 36 ± 9 | 39 ± 13 | 26 ± 12 | 19 ± 10 |
| pentoxifylline 50 μmol/l | | 28 ± 10 | | |
| test substance + pentoxifylline (50 μmol/l) | 82 ± 13 | 87 ± 21 | 63 ± 15 | 65 ± 19 |

Example 2 shows that the nifedipine used in Example 1 is also only representative of other so-called "calcium antagonists" and can be replaced with e.g. diltiazem, verapamil or cyclosporin A.

EXAMPLE 3

The PBMC fraction was further fractionated to give pure T lymphocytes. This was done using Lympho-KWIK-T, a mixture of monoclonal antibodies from anti-monocytes and anti-B cells and complement, together with a mixture of monoclonal anti-NK and anti-monocyte antibodies with Leu 11 b (anti-CD16, IgM) and Leu 7 (anti-CD57, IgM) (One Lambda Inc., Los Angeles. Calif., USA). The isolation and purification of the T lymphocytes from the PBMC fraction was effected by means of the following process steps:

Monocytes are removed by cold agglutination.

$30 \times 10^6$ of the cells obtained are incubated with 0.8 ml of Lympho-KWIK-T for 1 hour at 37° C.

The cells are washed three times and then incubated for 30 minutes at 4° C. with the mixture of monoclonal anti-NK and anti-monocyte antibodies.

The cells are washed once and re-incubated with 0.8 ml of Lympho-KWIK-T for 1 hour at 37° C.

The cells are washed three times and resuspended in culture medium (RPMI 1640; Gibco, Life Techn. GmbH).

The cell preparation obtained by this procedure contained more than 97% of T lymphocytes (CD3+), as determined by flow cytometry.

Test Procedure $5 \times 10^4$ T lymphocytes were incubated in a 5% $CO_2$ atmosphere at 37° C. in 200 μl of culture medium (RPMI 1640 supplemented with 10% of fetal calf serum, penicillin and streptomycin), in flat-bottomed microtiter plates, with monoclonal anti-CD3 or anti-CD28 antibodies (1 μg/ml of each of the monoclonal antibodies) and phorbol myristate acetate (PMA; Sigma, Switzerland; 5 ng/ml). The test substances (cyclosporin A 40 nmol/l to 100 nmol/l, pentoxifylline 2 μmol/l to 80 μmol/l, db-cAMP 0.01 μmol/l to 50 μmol/l) were added at time 0, individually or in combination. After 64 h of incubation the cells were treated in each case with 1 μCi of $^3$H-thymidine; 8 h later they were collected on glass fiber filters and the incorporated radioactivity was measured in a β counter.

The percentage inhibition of the T lymphocyte proliferation by the test substances was compared with a control not containing test substance, subtracting a basal value without monoclonal antibodies. The mean value from 4 parallel preparations was used for the evaluation. Table 3 shows the inhibition of the T lymphocyte proliferation by the test substances, individually or in combination, as a function of the type of lymphocyte activation.

TABLE 3

|  |  | % inhibition of proliferation Stimulation via | |
|---|---|---|---|
|  |  | CD3/PMA | CD28/PMA |
| Cyclosporin A | 20 nmol/l | 29 ± 4 | 9 ± 5 |
| Pentoxifylline | 40 μmol/l | 21 ± 7 | 28 ± 8 |
| db-cAMP | 0.1 μmol/l | 16 ± 6 | 11 ± 6 |
| Cyclosporin A + pentoxifylline | 20 nmol/l 40 μmol/l | 74 ± 14 | 68 ± 12 |
| Cyclosporin A + db-cAMP | 20 nmol/l 0.1 μmol/l | 63 ± 12 | 27 ± 13 |

Example 3 verifies that pentoxifylline not only acts as a PDE inhibitor by increasing cAMP, but also has a cAMP-independent active component, i.e. if T lymphocytes are activated not via the both cyclosporin A-sensitive and cAMP-sensitive CD3-dependent mechanism, but via the alternative CD28-dependent mechanism, pentoxifylline exhibits the same effects in both cases, even though cAMP remains practically inactive under the latter conditions. Of even greater interest in this Example is the finding that cyclosporin A, whose inactivity as a single substance in the stimulation of the T lymphocyte via CD28 is known, nevertheless again has a superadditive overall effect when combined with pentoxifylline, as in the case of stimulation via CD3, indicating that the effects in the combination have widened not only quantitatively but also qualitatively.

EXAMPLE 4

The effect of the topical application of a combination according to the invention to a single patient with pronounced psoriasis was studied in a parallel comparison. For this purpose the test substances pentoxifylline and diltiazem, dissolved in 30 ml of polypropylene glycol/ethanol/water ( 1:1:1, v/v), were incorporated, individually or together, in a final concentration of 2% (pentoxifylline) or 1% (diltiazem), into a commercially available creamy skin care product (Nivea lotion), ultimately giving the following 4 different formulations:

A) lotion without test substance (=vehicle control)
B) lotion with 2% of pentoxifylline
C) lotion with 1% of diltiazem
D) lotion with 2% of pentoxifylline +1% of diltiazem Twice a day for 6 weeks, these 4 formulations were applied locally, with rubbing, to areas of skin on the patient's trunk which were affected by pronounced symptoms of psoriasis and had previously been precisely defined, particular care being taken to ensure that the same formulation was always applied to the same area of skin. The therapeutic result was monitored visually and evaluated by means of the following subjective scores:

| Symptoms: | |
|---|---|
| completely disappeared | 5 |
| almost disappeared | 4 |
| markedly better* | 3 |
| slightly better* | 2 |
| scarcely better* | 1 |
| no change* | 0 |
| slightly worse* | -1 |
| markedly worse* | -2 |

*The reference point was always the original initial condition (i.e. week 0).

Table 4 shows the treatment result for all 4 formulations, as defined by the above scores, over the 6-week period of therapy.

TABLE 4

| Lotion | Week | | | | | | |
|---|---|---|---|---|---|---|---|
|  | 0 | 1 | 2 | 3 | 4 | 5 | 6 |
| A | — | 0 | 1 | 1 | 1 | 1 | 1 |
| B | — | 0 | 1 | 1 | 2 | 2 | 2 |
| C | — | 0 | 0 | 1 | 0 | 1 | 1 |
| D | — | 1 | 1 | 2 | 3 | 3 | 4 |

Example 4 shows that the combination according to the invention is active not only in vitro but also in vivo on humans. The topical application of pentoxifylline (so-called "PDE inhibitor") and diltiazem (so-called "calcium antagonist"), alone or in combination, showed marked differences between the vehicle (=placebo), the two single substances and the combination in a parallel comparison on one and the same patient suffering from psoriasis. Whereas after a 6-week application of both the vehicle and diltiazem there was practically no visible difference relative to the initial situation, and the symptoms had also improved only moderately under pentoxifylline alone, the area of skin treated with the combination showed an extensive disappearance of all the symptoms associated with psoriasis; only a residual redness of the affected areas of skin was still visible in the longer term. although this also continued to disappear gradually under further treatment and was practically no longer perceptible after 3 months.

We claim:

1. A method of treating psoriasis in a patient comprising topically administering pentoxifylline and diltiazem to said patient.

2. The method of claim 1, wherein said pentoxifylline and diltiazem are administered together in a single pharmaceutical composition to said patient.

3. The method of claim 1, wherein said pharmaceutical composition further comprises substances selected from the group consisting of animal and vegetable fats, waxes, paraffins, starch, gum tragacanth, cellulose derivatives, polyethylene glycols, silicones, bentonite, talcum, zinc oxide, lactose, silicic acid, aluminum hydroxide, calcium silicate, powdered polyamide and mixtures thereof.

4. The method of claim 2, wherein said pharmaceutical composition further comprises substances selected from the group consisting of animal and vegetable fats, waxes, paraffins, starch, gum tragacanth, cellulose derivatives, polyethylene glycols, silicones, bentonite, talcum, zinc oxide, lactose, silicic acid, aluminum hydroxide, calcium silicate, powdered polyamide and mixtures thereof.

5. The method of claim 1, wherein said pharmaceutical composition is administered to said patient for at least three weeks.

6. The method of claim 5, wherein said pharmaceutical composition is administered to said patient for at least four weeks.

7. The method of claim 2, wherein said pharmaceutical composition is administered to said patient for at least three weeks.

8. The method of claim 7, wherein said pharmaceutical composition is administered to said patient for at least four weeks.

* * * * *